(12) United States Patent
Liu et al.

(10) Patent No.: US 10,273,266 B2
(45) Date of Patent: Apr. 30, 2019

(54) MULTI-FUNCTIONAL PEPTIDE BENEFITING EXPRESSION, PURIFICATION, STABILIZATION AND CATALYTIC EFFICIENCY OF RECOMBINANT PROTEINS

(71) Applicant: Jiangnan University, Wuxi (CN)

(72) Inventors: Song Liu, Wuxi (CN); Weixin Zhao, Wuxi (CN); Jian Chen, Wuxi (CN); Guocheng Du, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 15/658,193

(22) Filed: Jul. 24, 2017

(65) Prior Publication Data
US 2018/0298058 A1  Oct. 18, 2018

(30) Foreign Application Priority Data
Apr. 14, 2017 (CN) .......................... 2017 1 0247285

(51) Int. Cl.
| | | |
|---|---|---|
| *C12N 9/00* | (2006.01) | |
| *C12N 5/00* | (2006.01) | |
| *C07K 19/00* | (2006.01) | |
| *C07K 1/04* | (2006.01) | |
| *C07K 7/08* | (2006.01) | |
| *C12N 9/88* | (2006.01) | |
| *C12N 9/02* | (2006.01) | |
| *C07K 14/00* | (2006.01) | |

(52) U.S. Cl.
CPC .............. *C07K 7/08* (2013.01); *C07K 14/00* (2013.01); *C12N 9/0069* (2013.01); *C12N 9/88* (2013.01); *C12Y 113/11012* (2013.01); *C12Y 402/02002* (2013.01); *C07K 2319/40* (2013.01); *C07K 2319/60* (2013.01)

(58) Field of Classification Search
CPC ........... C12P 21/06; C12N 1/00; C07K 14/00; C07K 14/605; C07K 14/57581
See application file for complete search history.

(56) References Cited

U.S. PATENT DOCUMENTS

| | | | | |
|---|---|---|---|---|
| 9,200,306 B2 * | 12/2015 | Lin | ........................ | C07K 14/00 |
| 9,308,277 B2 * | 4/2016 | Segers | ................. | C07K 14/522 |

* cited by examiner

*Primary Examiner* — Maryam Monshipouri
(74) *Attorney, Agent, or Firm* — Na Xu; IPro, PLLC (57) ABSTRACT

The present invention relates to a multi-functional peptide benefiting expression, purification, stabilization and catalytic efficiency of recombinant proteins, which relates to the field of enzyme engineering and protein purification. The present invention provides a self-assembling amphipathic peptide, which fused with proteins including alkaline polygalacturonate lyase (PGL), lipoxygenase (LOX) and green fluorescent protein (GFP), which leads to successful purification by the nickel affinity chromatography with recovery rates were 47.01%, 39.01% and 56.1%, respectively. Furthermore, the expression quantity and thermostability of the three proteins were enhanced in different degree. Of which the half-life of the PGL-S1v1 and LOX-S1v1 were 2.3 and 3.8-fold as compared with the corresponding wild-type and the specific activity were 1.1 and 1.9-fold increase, respectively. The crude enzyme activity of PGL-S1v1 was 9-fold increase than the PGL.

2 Claims, 2 Drawing Sheets

Specification includes a Sequence Listing.

SEQUENCE LISTING

```
<160> NUMBER OF SEQ ID NOS: 9

<210> SEQ ID NO 1
<211> LENGTH: 16
<212> TYPE: PRT
<213> ORGANISM: Artificial Sequence
<220> FEATURE:
<223> OTHER INFORMATION: Synthetic protein

<400> SEQUENCE: 1

Ala Glu Ala Glu Ala His Ala His Ala Glu Ala Glu Ala His Ala His
1               5                   10                  15

<210> SEQ ID NO 2
<211> LENGTH: 48
<212> TYPE: DNA
<213> ORGANISM: Artificial Sequence
<220> FEATURE:
<223> OTHER INFORMATION: Synthetic DNA

<400> SEQUENCE: 2
gcggaggcgg aagctcacgc tcatgcggag gcggaagctc acgctcat                 48

<210> SEQ ID NO 3
<211> LENGTH: 16
<212> TYPE: PRT
<213> ORGANISM: Artificial Sequence
<220> FEATURE:
<223> OTHER INFORMATION: Synthetic DNA

<400> SEQUENCE: 3

Pro Thr Pro Pro Thr Thr Pro Thr Pro Pro Thr Thr Pro Thr Pro Thr
1               5                   10                  15

<210> SEQ ID NO 4
<211> LENGTH: 1206
```

<212> TYPE: DNA
<213> ORGANISM: Artificial Sequence
<220> FEATURE:
<223> OTHER INFORMATION: Synthetic DNA

<400> SEQUENCE: 4

```
atggatgctg atttaggcca ccagacgttg ggatccaatg atggctgggg cgcgtactcg      60
accggcacga caggcgggtc aaaagcatcg tccttaaatg tgtataccgt cagcaacaga     120
aaccagcttg tctcggcatt agggaaggaa acgaacacaa cgccaaaaat catttatatc     180
aagggaacga ttgacatgaa cgtagatgac aatctgaagc cgcttggtct aaatgactat     240
aaagatccgg agtatgattt ggacaaatat ttgaaagcct atgatcctag acatggggc     300
aaaaaagagc cgtcgggaac acaagaagaa gcgagagcac gctctcagaa aaaccaaaaa     360
gcacgggtta tggtggatat ccctgcaaac acgacgatcg tcggttcagg gactaacgct     420
aaagtcgtgg aggaaacttt ccaaatcaag agtgataacg tcattattcg caacattgaa     480
ttccaggatg cctatgatta ttttccgcaa tgggatccga ctgacggaag ctcaggaaac     540
tggaactcac aatacgacaa catcacgata aacggcggca cacacatctg gattgatcac     600
tgtacattta cgacggttc gcgtccggac agcacatcac cgaaatatta tggaagaaaa     660
tatcagcacc atgacggcca aacggatgcg tccaacggcg ctaactatat cacgatgtcc     720
tacaactatt atcacgatca tgataaaagc tccattttcg gatcaagtga cagcaaaacc     780
tccgatgacg gcaaattaaa aattacgctc catcataacc gctataaaaa tattgtccag     840
cgcgcgccga gagtccgctt cgggcaagtg cacgtataca caactatta tgaaggaagc     900
acaagctctt caagttatcc tttcagctat gcatggggaa tcggaaagtc atctaaaatc     960
tatgcccaaa acaatgtcat tgacgtaccg ggactgtcag ctgctaaaac gatcagcgta    1020
ttcagcgggg gaacggcttt atatgactcc ggcacgttgc tgaacggcac acagatcaac    1080
gcatcggctg caaacgggct gagctcttct gtcggctgga cgccgtctct gcatggatcg    1140
attgatgctt ctgctaatgt gaaatcaaat gtcataaatc aagcgggtgc gggtaaatta    1200
aattaa                                                              1206
```

<210> SEQ ID NO 5
<211> LENGTH: 439
<212> TYPE: PRT
<213> ORGANISM: Artificial Sequence
<220> FEATURE:
<223> OTHER INFORMATION: Protein translated from synthetic DNA

<400> SEQUENCE: 5

```
Met Ala Glu Ala Glu Ala His Ala His Ala Glu Ala Glu Ala His Ala
1               5                   10                  15

His Trp Ile Ser Pro Thr Pro Thr Thr Thr Pro Thr Pro Thr Thr
            20                  25                  30

Pro Thr Pro Thr Pro Ala Met Asp Ala Asp Leu Gly His Gln Thr Leu
        35                  40                  45

Gly Ser Asn Asp Gly Trp Gly Ala Tyr Ser Thr Gly Thr Thr Gly Gly
    50                  55                  60

Ser Lys Ala Ser Ser Leu Asn Val Tyr Thr Val Ser Asn Arg Asn Gln
65                  70                  75                  80

Leu Val Ser Ala Leu Gly Lys Glu Thr Asn Thr Thr Pro Lys Ile Ile
                85                  90                  95

Tyr Ile Lys Gly Thr Ile Asp Met Asn Val Asp Asn Leu Lys Pro
            100                 105                 110
```

Leu Gly Leu Asn Asp Tyr Lys Asp Pro Glu Tyr Asp Leu Asp Lys Tyr
        115                 120                 125

Leu Lys Ala Tyr Asp Pro Ser Thr Trp Gly Lys Lys Glu Pro Ser Gly
130                 135                 140

Thr Gln Glu Glu Ala Arg Ala Arg Ser Gln Lys Asn Gln Lys Ala Arg
145                 150                 155                 160

Val Met Val Asp Ile Pro Ala Asn Thr Thr Ile Val Gly Ser Gly Thr
                165                 170                 175

Asn Ala Lys Val Val Gly Gly Asn Phe Gln Ile Lys Ser Asp Asn Val
                180                 185                 190

Ile Ile Arg Asn Ile Glu Phe Gln Asp Ala Tyr Asp Tyr Phe Pro Gln
                195                 200                 205

Trp Asp Pro Thr Asp Gly Ser Ser Gly Asn Trp Asn Ser Gln Tyr Asp
        210                 215                 220

Asn Ile Thr Ile Asn Gly Gly Thr His Ile Trp Ile Asp His Cys Thr
225                 230                 235                 240

Phe Asn Asp Gly Ser Arg Pro Asp Ser Thr Ser Pro Lys Tyr Tyr Gly
                245                 250                 255

Arg Lys Tyr Gln His His Asp Gly Gln Thr Asp Ala Ser Asn Gly Ala
                260                 265                 270

Asn Tyr Ile Thr Met Ser Tyr Asn Tyr His Asp His Asp Lys Ser
                275                 280                 285

Ser Ile Phe Gly Ser Ser Asp Ser Lys Thr Ser Asp Asp Gly Lys Leu
        290                 295                 300

Lys Ile Thr Leu His His Asn Arg Tyr Lys Asn Ile Val Gln Arg Ala
305                 310                 315                 320

Pro Arg Val Arg Phe Gly Gln Val His Val Tyr Asn Asn Tyr Tyr Glu
                325                 330                 335

Gly Ser Thr Ser Ser Ser Ser Tyr Pro Phe Ser Tyr Ala Trp Gly Ile
                340                 345                 350

Gly Lys Ser Ser Lys Ile Tyr Ala Gln Asn Asn Val Ile Asp Val Pro
                355                 360                 365

Gly Leu Ser Ala Ala Lys Thr Ile Ser Val Phe Ser Gly Gly Thr Ala
        370                 375                 380

Leu Tyr Asp Ser Gly Thr Leu Leu Asn Gly Thr Gln Ile Asn Ala Ser
385                 390                 395                 400

Ala Ala Asn Gly Leu Ser Ser Val Gly Trp Thr Pro Ser Leu His
                405                 410                 415

Gly Ser Ile Asp Ala Ser Ala Asn Val Lys Ser Asn Val Ile Asn Gln
                420                 425                 430

Ala Gly Ala Gly Lys Leu Asn
        435

<210> SEQ ID NO 6
<211> LENGTH: 2004
<212> TYPE: DNA
<213> ORGANISM: Artificial Sequence
<220> FEATURE:
<223> OTHER INFORMATION: Synthetic DNA

<400> SEQUENCE: 6
atgaatgact cgatattctt ttcacccttg aaatacctcg gggcggaaca acagcgatct    60
atcgatgcct cgcgaagttt gctggacaac ctgattccgc cgagtttgcc gcaatatgac    120
aacctggccg gaaagttggc gcggcgtgcg gtattgacca gcaagaaact ggtatatgtc    180

```
tggaccgaga acttcggcaa tgtcaaaggc gtgccgatgg cccgctcggt gccgctgggc    240
gagttgccga atgtcgactg gctgttgaag accgccgggg tgatcgtcga gctgatcgtc    300
aatttcgtcg cctcgttgcc ggcgtcggcc gcagcgcagt tcgagcggat cgccaccggg    360
ctcagcggtg acctggaggc ggcgcgccag gtccacgagg cgttgctgga ggaggcgaag    420
aacgatccgg ccgcggccgg cagcctgctg ctgcgcttca cggagttgca gacgcgggtg    480
atcgccatac tgacgcgggt cggcctgctg gtcgacgata ttctcaagag cgccagcaac    540
ctggttaccc agagggggca gggcgacggc ctgaatcgct tccgcgcggt gttcggcacc    600
ctgcgcctgc cggaggtcgc cgacagcttc cgtgacgacg aagcgttcgc ctactggcgg    660
gtggccgggc taatccgct gctgatccgt cgcgtcgatg cgctgccggc caactttccg    720
ctgggcgagg agcagttccg ccgggtgatg ggcgccgacg acagcttgct ggaggccgcc    780
gccagccgcc gcctgtatct gctggactac gccgagctgg gcaagctggc gccgtcggga    840
gcggtggaca aactgctcac cgggacgggc ttcgcctatg cgccgatcgc cctgttcgcc    900
cttggcaagg atcgggcgag gctattgccg gtggccatcc agtgcggtca ggaccccgct    960
acccatccga tgttcgtgcg tcccgccgag tcggagagtg atctgtactg gggttggcag   1020
atggccaaga cggtggtcca ggtcgccgag gagaactacc acgagatgtt cgtccacctg   1080
gcccagaccc acctggtgag cgaggcgttc tgcctggcca cccagcgcac cctggcgccc   1140
agccatccgc tgcacgtcct gctcgccccg cacttcgagg gcaccctgtt catcaacgag   1200
ggggcggcgc gtatcctgtt gcccagcgcg ggcttcatcg acgtgatgtt cgccgcgccg   1260
atccaggaca cccaggccac cgccggcggc aatcggctgg gtttcgactt ctaccgcggc   1320
atgttgccgg agagcctgaa ggcgcggaac gtcgacgacc cgctggcgct accggactac   1380
ccctatcgcg acgacggcct gctggtatgg aatgccatcc gccagtgggc ggccgactac   1440
gtggcggtgt actacgccag cgacggcgac gtcaccgctg acgtcgaact gcggcctgg    1500 gtcggcgaag tgatcggcag cggcaaggtg gccgggttcc gcccgatcac cggtcgcagc   1560
caactggtcg aggtgctgac gatggtgatc ttcactgcct ccgcgcaaca tgcggcggtc   1620
aattttcccc agccttcgat gatgacctac gcaccagcca tctgtgccat gagcgcggcg   1680
ccggcaccgg actcgccaag cggcaagagc gaggccgatt ggttgaagat gatgccgccg   1740
accctggtgg cgctggagaa ggtgaacatc tatcacctgc tcggttcggt ctaccacggt   1800
cgcctgggcg actaccggca gaccgggttc ccctacgcgc cggtgttttc ggacaggcgg   1860
gtgaccgcca gcggcggccc gctggagcgc ttccaggcac gcctgaagga ggtcgaggcg   1920
accattcgca cgcgcaacca ggcgcgccgc aggccctacg agtacctgtt gccgagccgt   1980
atcccggcga gcaccaatat ctga                                         2004
```

<210> SEQ ID NO 7
<211> LENGTH: 706
<212> TYPE: PRT
<213> ORGANISM: Artificial Sequence
<220> FEATURE:
<223> OTHER INFORMATION: Protein translated from synthetic DNA

<400> SEQUENCE: 7

Met Ala Glu Ala Glu Ala His Ala His Ala Glu Ala Glu Ala His Ala
1               5                   10                  15

His Trp Ile Ser Pro Thr Pro Pro Thr Thr Pro Thr Pro Pro Thr Thr
                20                  25                  30

```
Pro Thr Pro Thr Pro Ala Met Asp Asn Asp Ser Ile Phe Phe Ser Pro
             35                  40                  45

Leu Lys Tyr Leu Gly Ala Glu Gln Gln Arg Ser Ile Asp Ala Ser Arg
 50                  55                  60

Ser Leu Leu Asp Asn Leu Ile Pro Pro Ser Leu Pro Gln Tyr Asp Asn
 65                  70                  75                  80

Leu Ala Gly Lys Leu Ala Arg Arg Ala Val Leu Thr Ser Lys Lys Leu
                 85                  90                  95

Val Tyr Val Trp Thr Glu Asn Phe Gly Asn Val Lys Gly Val Pro Met
                100                 105                 110

Ala Arg Ser Val Pro Leu Gly Glu Leu Pro Asn Val Asp Trp Leu Leu
             115                 120                 125

Lys Thr Ala Gly Val Ile Val Glu Leu Ile Val Asn Phe Val Ala Ser
130                 135                 140

Leu Pro Ala Ser Ala Ala Gln Phe Glu Arg Ile Ala Thr Gly Leu
145                 150                 155                 160

Ser Gly Asp Leu Glu Ala Ala Arg Gln Val His Glu Ala Leu Leu Glu
                165                 170                 175

Glu Ala Lys Asn Asp Pro Ala Ala Gly Ser Leu Leu Arg Phe
             180                 185                 190

Thr Glu Leu Gln Thr Arg Val Ile Ala Ile Leu Thr Arg Val Gly Leu
         195                 200                 205

Leu Val Asp Asp Ile Leu Lys Ser Ala Ser Asn Leu Val Thr Gln Arg
         210                 215                 220

Gly Gln Gly Asp Gly Leu Asn Arg Phe Arg Ala Val Phe Gly Thr Leu
225                 230                 235                 240

Arg Leu Pro Glu Val Ala Asp Ser Phe Arg Asp Asp Glu Ala Phe Ala
             245                 250                 255

Tyr Trp Arg Val Ala Gly Pro Asn Pro Leu Leu Ile Arg Arg Val Asp
             260                 265                 270

Ala Leu Pro Ala Asn Phe Pro Leu Gly Glu Gln Phe Arg Arg Val
             275                 280                 285

Met Gly Ala Asp Asp Ser Leu Leu Glu Ala Ala Ser Arg Arg Leu
290                 295                 300

Tyr Leu Leu Asp Tyr Ala Glu Leu Gly Lys Leu Ala Pro Ser Gly Ala
305                 310                 315                 320

Val Asp Lys Leu Leu Thr Gly Thr Gly Phe Ala Tyr Ala Pro Ile Ala
                 325                 330                 335

Leu Phe Ala Leu Gly Lys Asp Arg Ala Arg Leu Leu Pro Val Ala Ile
             340                 345                 350

Gln Cys Gly Gln Asp Pro Ala Thr His Pro Met Phe Val Arg Pro Ala
         355                 360                 365

Glu Ser Glu Ser Asp Leu Tyr Trp Gly Trp Gln Met Ala Lys Thr Val
370                 375                 380

Val Gln Val Ala Glu Glu Asn Tyr His Glu Met Phe Val His Leu Ala
385                 390                 395                 400

Gln Thr His Leu Val Ser Glu Ala Phe Cys Leu Ala Thr Gln Arg Thr
             405                 410                 415

Leu Ala Pro Ser His Pro Leu His Val Leu Leu Ala Pro His Phe Glu
                 420                 425                 430

Gly Thr Leu Phe Ile Asn Glu Gly Ala Ala Arg Ile Leu Leu Pro Ser
             435                 440                 445

Ala Gly Phe Ile Asp Val Met Phe Ala Ala Pro Ile Gln Asp Thr Gln
```

```
                    450                 455                 460
Ala Thr Ala Gly Gly Asn Arg Leu Gly Phe Asp Phe Tyr Arg Gly Met
465                 470                 475                 480

Leu Pro Glu Ser Leu Lys Ala Arg Asn Val Asp Asp Pro Leu Ala Leu
                485                 490                 495

Pro Asp Tyr Pro Tyr Arg Asp Asp Gly Leu Leu Val Trp Asn Ala Ile
            500                 505                 510

Arg Gln Trp Ala Ala Asp Tyr Val Ala Val Tyr Tyr Ala Ser Asp Gly
        515                 520                 525

Asp Val Thr Ala Asp Val Glu Leu Ala Ala Trp Val Gly Glu Val Ile
    530                 535                 540

Gly Ser Gly Lys Val Ala Gly Phe Arg Pro Ile Thr Gly Arg Ser Gln
545                 550                 555                 560

Leu Val Glu Val Leu Thr Met Val Ile Phe Thr Ala Ser Ala Gln His
                565                 570                 575

Ala Ala Val Asn Phe Pro Gln Pro Ser Met Met Thr Tyr Ala Pro Ala
            580                 585                 590

Ile Cys Ala Met Ser Ala Ala Pro Ala Pro Asp Ser Pro Ser Gly Lys
        595                 600                 605

Ser Glu Ala Asp Trp Leu Lys Met Met Pro Pro Thr Leu Val Ala Leu
    610                 615                 620

Glu Lys Val Asn Ile Tyr His Leu Leu Gly Ser Val Tyr His Gly Arg
625                 630                 635                 640

Leu Gly Asp Tyr Arg Gln Thr Gly Phe Pro Tyr Ala Pro Val Phe Ser
                645                 650                 655

Asp Arg Arg Val Thr Ala Ser Gly Gly Pro Leu Glu Arg Phe Gln Ala
            660                 665                 670

Arg Leu Lys Glu Val Glu Ala Thr Ile Arg Thr Arg Asn Gln Ala Arg
        675                 680                 685

Arg Arg Pro Tyr Glu Tyr Leu Leu Pro Ser Arg Ile Pro Ala Ser Thr
    690                 695                 700

Asn Ile
705

<210> SEQ ID NO 8
<211> LENGTH: 717
<212> TYPE: DNA
<213> ORGANISM: Artificial Sequence
<220> FEATURE:
<223> OTHER INFORMATION: Synthetic DNA

<400> SEQUENCE: 8
atgggtaagg gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaagcttc ctgttccttg gccaacactt     180
gtcactactc ttacttatgg tgttcaatgc ttttcaagat acccagatca tatgaagcgg     240
cacgacttct tcaagagcgc catgcctgag ggatacgtgc aggagaggac catcttcttc     300
aaggacgacg gaactacaa gacacgtgct gaagtcaagt tgagggaga caccctcgtc     360 aacagaatcg agcttaaggg aatcgatttc aaggaggacg gaaacatcct cggccacaag     420
ttggaataca actacaactc ccacaacgta tacatcatgg cagacaaaca aaagaatgga     480
atcaaagtta acttcaaaat tagacacaac attgaagatg gaagcgttca actagcagac     540
cattatcaac aaaatactcc aattggcgat ggccctgtcc ttttaccaga caaccattac     600
```
ctgtccacac aatctgccct ttcgaaagat cccaacgaaa agagagacca catggtcctt    660
cttgagtttg taacagctgc tgggattaca catggcatgg atgaactata caaataa      717

<210> SEQ ID NO 9
<211> LENGTH: 275
<212> TYPE: PRT
<213> ORGANISM: Artificial Sequence
<220> FEATURE:
<223> OTHER INFORMATION: Protein translated from synthetic DNA

<400> SEQUENCE: 9

Met Ala Glu Ala Glu Ala His Ala His Ala Glu Ala Glu Ala His Ala
1               5                   10                  15

His Trp Ile Ser Pro Thr Pro Pro Thr Thr Pro Thr Pro Pro Thr Thr
            20                  25                  30

Pro Thr Pro Thr Pro Met Gly Lys Gly Glu Glu Leu Phe Thr Gly Val
        35                  40                  45

Val Pro Ile Leu Val Glu Leu Asp Gly Asp Val Asn Gly His Lys Phe
    50                  55                  60

Ser Val Ser Gly Glu Gly Glu Gly Asp Ala Thr Tyr Gly Lys Leu Thr
65                  70                  75                  80

Leu Lys Phe Ile Cys Thr Thr Gly Lys Leu Pro Val Pro Trp Pro Thr
                85                  90                  95

Leu Val Thr Thr Leu Thr Tyr Gly Val Gln Cys Phe Ser Arg Tyr Pro
            100                 105                 110

Asp His Met Lys Arg His Asp Phe Phe Lys Ser Ala Met Pro Glu Gly
        115                 120                 125

Tyr Val Gln Glu Arg Thr Ile Phe Phe Lys Asp Asp Gly Asn Tyr Lys
    130                 135                 140

Thr Arg Ala Glu Val Lys Phe Glu Gly Asp Thr Leu Val Asn Arg Ile
145                 150                 155                 160

Glu Leu Lys Gly Ile Asp Phe Lys Glu Asp Gly Asn Ile Leu Gly His
                165                 170                 175

Lys Leu Glu Tyr Asn Tyr Asn Ser His Asn Val Tyr Ile Met Ala Asp
            180                 185                 190

Lys Gln Lys Asn Gly Ile Lys Val Asn Phe Lys Ile Arg His Asn Ile
        195                 200                 205

Glu Asp Gly Ser Val Gln Leu Ala Asp His Tyr Gln Gln Asn Thr Pro
    210                 215                 220

Ile Gly Asp Gly Pro Val Leu Leu Pro Asp Asn His Tyr Leu Ser Thr
225                 230                 235                 240

Gln Ser Ala Leu Ser Lys Asp Pro Asn Glu Lys Arg Asp His Met Val
                245                 250                 255

Leu Leu Glu Phe Val Thr Ala Ala Gly Ile Thr His Gly Met Tyr Glu
            260                 265                 270

Leu Tyr Lys
        275

MULTI-FUNCTIONAL PEPTIDE BENEFITING EXPRESSION, PURIFICATION, STABILIZATION AND CATALYTIC EFFICIENCY OF RECOMBINANT PROTEINS

CROSS-REFERENCES AND RELATED APPLICATIONS

This application claims the benefit of priority to Chinese Application No. 201710247285.2, entitled "A self-assembling amphipathic peptide and its application", filed Apr. 14, 2017, which is herein incorporated by reference in its entirety.

BACKGROUND OF THE INVENTION

Field of the Invention

The present invention relates to a multi-functional peptide benefiting expression, purification, stabilization and catalytic efficiency of recombinant proteins, which relates to the field of enzyme engineering and protein purification.

Description of the Related Art

Self-assembling amphipathic peptides (SAPs) are kinds of functional peptides, which have alternating hydrophilic and hydrophobic residues and can aggregate into ordered nano-structures spontaneously in solution. In the field of nanotechnology, SAPs have great potential applications in areas such as biomedical nanotechnology, cell culturing, and molecular electronics. They have also been used as additives to protect membrane proteins from aggregation during protein expression, purification, and crystallization. Inspired from the application of additives, SAPs had been firstly fused to the N-terminus of *Pseudomonas aeruginosa* lipoxygenase and improved the thermostability of the fusion enzyme and other properties. Then the α-amylase, pectinase and nitrile hydratase benefited in succession. In addition, SAPs have been anchored to the plant cytochrome CYP73A1 to enhance the water solubility. Which illustrated the functional diversity and potential of SAPs to be developed into a sort of multifunctional tags.

Purification of proteins with His-tag is the most commonly used method of which poly-histidine affinity tags are commonly placed on either the N- or the C-terminus of recombinant proteins. Proteins containing relative consecutive histidine residues can be efficiently retained on immobilized metal-affinity chromatography and easily eluted by either adjusting the pH of the column buffer or by adding free imidazole. However, some kinds of the enzyme protein molecules possess the end which embedded in the molecules, the histidine tag cannot be trapped on the surface of the enzyme molecule, so that the method cannot be used for purification of the enzyme.

DETAILED DESCRIPTION

In this invention, a self-assembling amphipathic peptide (S1v1, AEAEAHAHAEAEAHAH) was applied in fusing to recombinant proteins, including alkaline polygalacturonate lyase (PGL, EC 4.2.2.2), lipoxygenase (LOX, EC 1.13.11.12) and green fluorescent protein (GFP), which demonstrated the feasibility of universal application. All of the three fusion proteins were purified successfully by affinity chromatography, in addition, the thermal stability, expression quantity and other enzymatic properties were enhanced in different degree.

The first goal of the present invention is to provide a self-assembling amphipathic peptide with multifunction application, wherein the peptide comprises an amino acid sequence as shown in SEQ ID NO.1 and the nucleotide sequence as shown in SEQ ID NO.2.

The second goal of the present invention is to provide a method of producing the proteins by fused expressing the self-assembling amphipathic peptide with the recombinant proteins.

In one embodiment of the present invention, the multi-functional self-assembling amphipathic peptide is used as a purification tag for the fused proteins or enzymes.

In one embodiment of the present invention, the multi-functional self-assembling amphipathic peptide is used to enhanced the expression quantity of the fused proteins or enzymes.

In one embodiment of the present invention, the multi-functional self-assembling amphipathic peptide is used to improve the thermal stability of the fused proteins or enzymes.

In one embodiment of the present invention, the multi-functional self-assembling amphipathic peptide is used to improve the catalytic efficiency of the fused proteins or enzymes.

In one embodiment of the present invention, the wherein said fused expressing is carried out from ligating the self-assembled peptide with to the N-terminus or C-terminus of the protein and then expressing the protein that were fused by self-assembling amphipathic peptide.

In one embodiment of the present invention, the proteins that were fused by self-assembling amphipathic peptide are the bioactive enzymes or proteins.

In one embodiment of the present invention, the proteins that were fused by self-assembling amphipathic peptide included oxidase, transferase, hydrolase, polymerase, isomerase or ligase.

In one embodiment of the present invention, the linker peptide is used to connect the self-assembling amphipathic peptide and proteins.

In one embodiment of the present invention, the linker peptide is PT-linker which comprises an amino acid sequence as shown in SEQ ID NO.3.

In one embodiment of the present invention, the operating steps of the method is: (1) the nucleotide sequence of the self-assembling amphipathic peptide is synthesized according to SEQ ID NO.2 and then cloned into the expression vector; (2) the gene encoding the target protein was cloned to the expression vector as constructed by step (1), then the recombinant expression vector was constructed; (3) The recombinant expression vector was transformed into the target cells.

In one embodiment of the present invention, the target cells including *Escherichia coli* BL21 (DE3), or *E. coli* DH5α, or *E. coli* TOP 10, or *E. coli* Rosetta (DE3).

The present invention provides a self-assembling amphipathic peptide, which fused with proteins including alkaline polygalacturonate lyase (PGL), lipoxygenase (LOX) and green fluorescent protein (GFP), leading to successful purification by the nickel affinity chromatography with recovery rates were 47.01%, 39.01% and 56.1%, respectively. Furthermore, the expression quantity and thermostability of the three proteins were enhanced in different degree. Of which the half-life of the PGL-S1v1 and LOX-S1v1 were 2.3 and 3.8-fold as compared with the corresponding wild-type and the specific activity were 1.1 and 1.9-fold increase, respectively. The crude enzyme activity of PGL-S1v1 was 9-fold increase than the PGL.

BRIEF DESCRIPTION OF DRAWINGS

Figure Captions

DETAILED DESCRIPTION

Materials and Methods:
Strains and Plasmids:
The nucleotide sequence of PGL gene from *Bacillus subtilis* WSHB04-02 is shown as SEQ ID NO.4. The nucleotide sequence of LOX gene from *Pseudomonas aeruginosa* BBE is shown as SEQ ID NO.6. The nucleotide sequence of GFP gene from *Aequorea victoria* is shown as SEQ ID NO.8. *E. coli* JM109 was used as the host strain for cloning. *E. coli* BL21 (DE3) and *E. coli* Rosetta (DE3) were used as the expression hosts. The pET-22b (+) plasmid was used for expressing the recombinant proteins.

Primers used for amplifying the genes were shown in table 1.

TABLE 1

Oligonucleotides used in this study.

| Primer | Sequence (5'-3') | products |
|---|---|---|
| PGL-R | CTAG<u>CCATGG</u>ATGGATGCTGATTTAGGCCAC | pgl |
| PGL-F | CCG<u>CTCGAG</u>TTAATTTAATTTACCCGCAC | pgl |
| LOX-R | CTAG<u>CCATGG</u>AATGACTCGATATTCT | lox |
| LOX-F | CCG<u>CTCGAG</u>TGCGGCCGCAAGCTTTCAG | lox |
| GFP-R | CTAG<u>CCATGG</u>ATGGGTAAGGGAGAAGAAC | gfP |
| GFP-F | CCG<u>CTCGAG</u>TTATTTGTATAGTTCATCCATGCCATG | gfP |

Underlined bases represent enzyme restriction sites.

Medium:
Seed medium: peptone 10 g/L, yeast extract 5 g/L, NaCl 10 g/L, glucose 20 g/L, pH was adjusted to 7.0.
Fermentation medium: peptone 12 g/L, yeast extract 24 g/L, glycerol 5 g/L, $K_2HPO_4$ 72 mmol/L, $KH_2PO_4$ 17 mmol/L, pH 7.0.

Culture Conditions:
The *E. coli* BL21 (DE3) cells harboring the corresponding plasmid were cultured in Luria-Bertani (LB) medium with 2% glucose and 100 μg/mL ampicillin supplemented at 37° C., 220 rpm shaking, respectively. And single colony of *E. coli* Rosetta (DE3) cells harboring plasmid pET-22b(+)/lox-S1v1 and pET-22b(+)/lox-His-tag was inoculated into 25 mL LB medium containing 34 μg/mL chloramphenicol and 100 μg/mL ampicillin at 37° C., 220 rpm shaking, respectively. After overnight culturing, strains were inoculated into 25 ml of terrific broth (TB) which contained the same content of antibiotics as the corresponding seed culture and incubated at 37° C. with 220 rpm. When the optical density of bacterial concentration at 600 nm reached 0.6~0.8, proteins production were induced by isopropyl β-D-1-thiogalactopyranoside (IPTG) and cultured at the corresponding induction temperature, with shaking at 220 rpm. Induction conditions were: PGL: IPTG was added to a final concentration of 0.04 mM, 30° C., and 48 h induction culture; LOX: 1 mM IPTG, 20° C., 24 h; GFP: 0.05 mM IPTG, 20° C., 24 h.

Purification of the Recombinant Proteins:
The culture supernatant containing the PGL was obtained by centrifugation at 9,000×g for 15 min. The cells contain LOX and GFP were harvested by centrifugation and pellets were re-suspended in buffer A (50 mM phosphate buffer [pH 7.4]) to 10 $OD_{600}$ culture/mL, followed by sonication (Ultrasonic crasher; Bannuo FS-1200, Shanghai, China). The soluble fractions were isolated from the aggregates by centrifugation at 10,000×g for 15 min at 4° C. After filtering through a Millipore filter (0.22 μm) in prior of the purification, the samples were injected into a His trap FF Crude (5 mL) by using an AKTA purifier (GE Healthcare, Houston, Tex.). The column was washed with 20% ethanol to remove impurities and equilibrated with buffer A1 (50 mM phosphate buffer [pH 7.4] containing 0.3 M NaCl and 20 mM imidazole). The flow rate of the sample application was 2.0 ml/min. After eluting the unbound proteins with the buffer A1 at the flow rate of 3.0 mL/min, proteins were eluted with a linear gradient from 0% to 100% buffer B (50 mM phosphate buffer [pH 7.4] containing 0.3 M NaCl and 500 mM imidazole). Those eluted fractions with target proteins were subjected to the desalting column (5 mL) with buffer A at the flow rate of 2.0 mL/min to remove the NaCl and imidazole. Fractions were collected for activity assays and analyzed by sodium dodecyl sulfate polyacrylamide gel electrophoresis (SDS-PAGE).

Enzyme Assay:

The polygalacturonate lyase (PGL) was determined by measuring the absorbance of unsaturated bonds between C4 and C5 at 235 nm. The reaction mixture contained 2 mL of 0.2% (w/v) polygalacturonic acid (Sigma Chemical Co. type P7276) in 200 mM glycine-NaOH buffer at pH 9.4 (containing 200 mM glycine, 200 mM NaOH, and 60 mM $CaCl_2$) and 20 μL of diluted enzyme solution. The reaction mixture was incubated at 45° C. for 15 min, and then the reaction was terminated by adding 3 mL of 30 mM phosphoric acid. The product was checked by a spectrophotometer (UV-2450; Shimadzu Co., Kyoto, Japan). One enzyme units is defined as formation of 1 μmol unsaturated polygalacturonic acid per min, with a molar extinction coefficient of 4600.

Linoleic acid was dispersed in 0.15 M $K_2HPO_4$—$KH_2PO_4$ buffer (pH 7.5). The substrate solution was freshly prepared daily and saturated with oxygen for 5 min before testing. Standard analytical mixture (3 mL) contains 0.3 mM linoleic acid and about 1.67 μg/mL enzyme. One unit of activity was defined as enzyme required to synthesis 1 μmol hydroperoxide per min at 25° C. Hydroperoxidaton was determined at 234 nm in a spectrophotometer (UV-2450; Shimadzu Co., Kyoto, Japan). The initial linear part of the wave was used to calculate enzyme activity.

The Fluorescent Spectral Properties Analyses:

The fluorescence was recorded using Cytation 3 imaging reader (BioTek, Winooski, Vt., USA) with excitation at 485 nm and emission at 515 nm, respectively. To determine the specific fluorescence activities of the green fluorescent protein (GFP), the samples of the equivalent protein concentration were detected.

Measurement of Enzyme Kinetics Stabilities:

The dynamic thermal stabilities of the PGL and LOX were determined by measuring the residual activity after incubating the enzyme solution at 60° C. and 50° C. in buffer A (50 mM phosphate buffer [pH 7.4]), respectively. Then the half-life was calculated using exponential fitting of the data points as previously described. The data were analyzed by fitting to first-order plots and the first-order rate constants ($k_d$) were determined by linear regression of ln (residual activity) versus the incubation time (t). The time required for the residual activity to be reduced to half ($t_{1/2}$) of the enzyme was calculated by the following equation: $t_{1/2}=\ln 2/k_d$.

The Fluorescent Spectral Properties Analyses:

To assess the thermal stability of GFP and GFP-S1v1, protein samples were diluted in buffer A to prepare initial solution of equal protein concentration and incubated 5 min at different temperatures from 65° C. to 90° C. at 5° C. intervals. The fluorescence remaining after heat treatment was measured and plotted as a function of temperature. As for the time-dependent assay, samples were incubated at 75° C. for 50 min with 10 min time intervals to record the remaining fluorescence.

Example 1

(1) The nucleotide sequence (as shown in SEQ ID NO. 2) encoding the self-assembling amphipathic peptide (S1v1, amino acids sequence is shown in SEQ ID NO.1) was synthesized and cloned into pET-22b(+) between the restriction EcoRI and NcoI sites for expression, which constructed the recombinant vector pET-22b(+)/S1v1.

(2) The PGL gene (shown in SEQ ID NO. 4) was cloned into the recombinant vector pET-22b(+)/S1v1 at the restriction NcoI and XhoI sites to construct a recombinant plasmid pET-22b(+)/pgl-S1v1;

(3) The recombinant plasmid pET-22b (+)/S1v1-PGL was transformed into host E. coli BL21 (DE3) to construct the recombinant strain E. coli BL21 (DE3) pET-22b (+)/pgl-S1v1.

Figure 1:
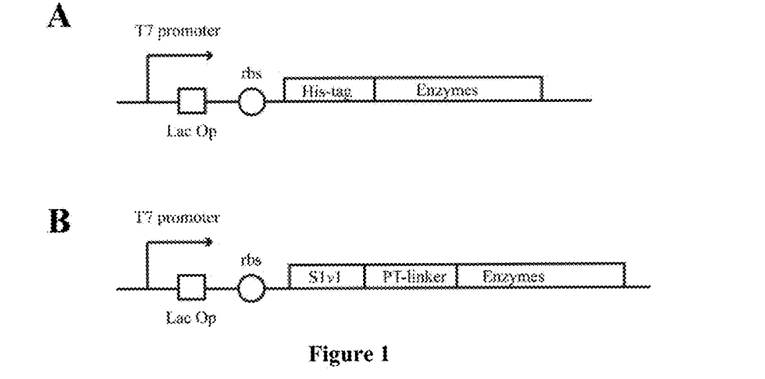
FIG. 1. (A) Genetic constructs of the His-tag fusion proteins; (B) Genetic constructs of the S1v1 fusion proteins. S1v1, AEAEAHAHAEAEAHAH; linker, PTPPTTPT-PPTTPTPT; His-tag, HHHHHH; Enzymes represented the encoding gene of three proteins (pgl, lox and gfp, respectively) used in this study.
Figure 2:
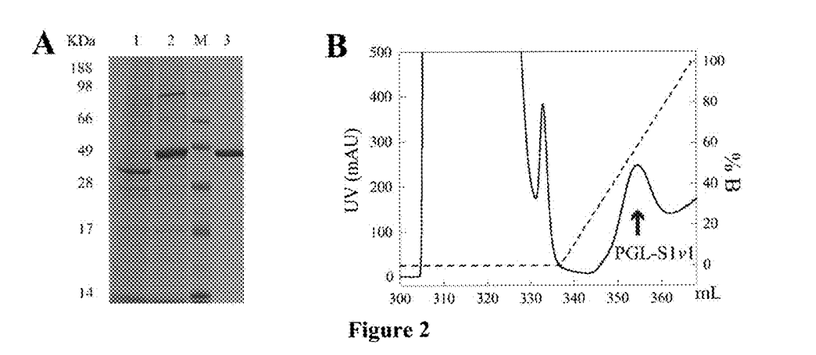
FIG. 2. (A) SDS-PAGE analysis of the purified PGL-S1v1 and the extracellular expression quantity PGL and PGL-S1v1; 1, culture supernatant of PGL; 2, culture supernatant of PGL-S1v1; M, molecular mass marker; 3, purified PGL-S1v1. (B) The Nickel column affinity chromatography of PGL-S1v1.

(4) The recombinant E. coli BL21 (DE3) pET-22b(+)/S1v1-PGL were inoculated and incubated. The IPTG was concentration of 0.04 mM was added to induced the PGL expression at 30° C. for 48 h. The culture broth was centrifuged and the fermentation supernatant was collected. The proteins in supernatant were purified and analyzed through SDS-PAGE The recombinant PGL-S1v1 was purified to homogeneity by nickel affinity chromatography (FIG. 2) from culture supernatant of E. coli BL21 (DE3) harboring pET-22b (+)/pgl-S1v1. However, the wild-type PGL with the His-tag in the N-terminal could not attached to the $Ni^{2+}$ affinity column, which was probably due to the N-terminal of the PGL protein was encased. The desalting column was applied to remove the NaCl and imidazole from the purified PGL-S1v1. SDS-PAGE analysis indicated that the recombinant PGL was purified to homogeneity after the purification by nickel affinity chromatography (FIG. 2A, lane 3), and the molecular weight of the PGL-S1v1 was about 48 kDa, Besides, the crude enzyme activity of the PGL-S1v1 was 9-fold than that of PGL. As summarized in Table 2, the specific activity of the purified PGL was 761.74 U/mg protein, and the purification yield was approximately 47%.

TABLE 2

Purification steps of the PGL-S1v1 from E. coli

| step | Total protein (mg) | Total activity (U) | Specific activity (U · mg$^{-1}$) | Yield (%) |
|---|---|---|---|---|
| Crude extract | 58.47 | 4212.4 | 72.04 | 100 |
| His Trap SP FF | 2.56 | 1980.4 | 761.74 | 47.01 |

The results of measurement of enzyme kinetics stabilities showed that, the $k_{cat}$ value of PGL-S1v1 was increased by 3.6-fold. The catalytic efficiencies ($k_{cat}/K_m$) of PGL-S1v1 was also enhanced. Consequently, the specific activity of PGL-S1v1 was 1.1-fold higher than that of PGL. After fusing the S1v1, the half-time exhibited a 1.3-fold increase at 60° C., indicating the enhanced kinetic stability of PGL fused with S1v1 (Table 3).

TABLE 3

Enzymatic properties of the wild-type PGL and the fusion proteins

| Enzyme | Value ± SD | | | | | |
|---|---|---|---|---|---|---|
| | Km (g/L) | kcat (min$^{-1}$) | kcat/Km (L/g · min) | Specific activity (U · mg$^{-1}$) | crude enzyme activity (U · mL$^{-1}$) | half-life ($t_{1/2}$, min) |
| PGL | 0.27 ± 0.011 | 12.69 ± 0.41 | 47 ± 1.22 | 279.14 ± 8.96 | 131.2 ± 2.1 | 5.2 ± 0.41 |
| PGL-His | 0.3 ± 0.01 | 13.21 ± 0.76 | 44.03 ± 0.9 | 267.66 ± 9.77 | 129.4 ± 5.78 | 5.4 ± 0.32 |
| PGL-Slvl | 0.76 ± 0.12 | 45.87 ± 3.22 | 60.35 ± 2.54 | 587.39 ± 1.14 | 1330 ± 13.1 | 11.85 ± 1.2 |

Example 2

(1) The nucleotide sequence (as shown in SEQ ID NO. 2) encoding the self-assembling amphipathic peptide (S1v1, amino acids sequence is shown in SEQ ID NO.1) was synthesized and cloned into pET-22b(+) between the restriction EcoRI and NcoI sites for expression, which constructed the recombinant vector pET-22b(+)/S1v1.

(2) The LOX gene (shown in SEQ ID NO. 6) was cloned into the recombinant vector pET-22b(+)/S1v1 at the restriction NcoI and XhoI sites to construct a recombinant plasmid pET-22b(+)/lox-S1v1.

(3) The recombinant plasmid pET-22b (+)/lox-S1v1 was transformed into host E. coli Rosetta (DE3) to construct the recombinant strain E. coli Rosetta (DE3) pET-22b (+)/lox-S1v1.

(4) The recombinant E. coli Rosetta (DE3) pET-22b(+)/lox-S1v1 were inoculated and incubated. The IPTG was concentration of 1 mM was added to induced the LOX expression at 20° C. for 24 h. The culture broth was centrifuged. Cells were collected and broke before centrifugation, supernatant was obtained for purification and enzyme analysis.

Figure 3:
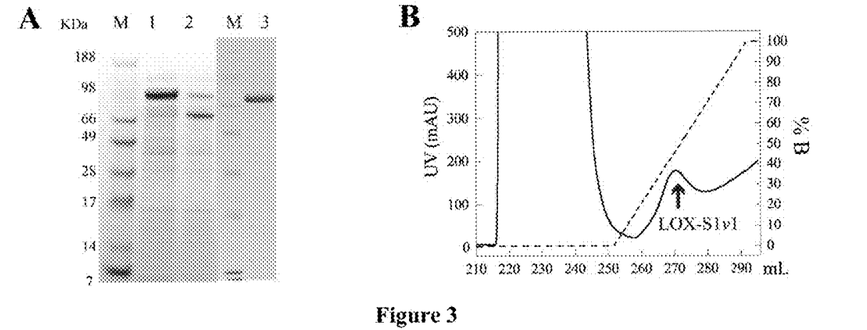
FIG. 3. (A) SDS-PAGE analysis of the purified LOX-S1v1 and the intracellular expression quantity of LOX and LOX-S1v1; M, molecular mass marker; 1, intracellular soluble of LOX-S1v1; 2, intracellular soluble of LOX; 3, the purified LOX-S1v1. (B) The Nickel column affinity chromatography of LOX-S1v1.

As shown in FIG. 3A, the molecular weight of LOX and LOX-S1v1 were 70 and 75 kDa, respectively. The expression quantity of the fusion proteins were significantly improved than that of wild-types. The fusion proteins were obviously expressed highly than that of the wild-types under the same conditions.

Due to the low expression quantity and poor thermostability, the wild-type LOX was unable to be purified by the nickel affinity column under the same purification condition without the procedures of concentration or glycerol addition. In previous study, when the LOX was fused to the other SAPs, only about 10% enzymes could be attached to the nickel affinity column, which was probably due to the interference from the fused SAPs. However, LOX-S1v1 presented relatively high affinity (FIG. 3B) and the purification yield was approximately 40% (Table 4). SDS-PAGE analysis indicated that the recombinant LOX-S1v1 was purified to homogeneity after the purification by nickel affinity chromatography (FIG. 3A, lane 3), and the molecular weight was about 75 kDa.

TABLE 4

Purification steps of the LOX-S1v1 from E. coli

| step | Total protein (mg) | Total activity (U) | Specific activity (U · mg$^{-1}$) | Yield (%) |
|---|---|---|---|---|
| Crude extract | 29.67 | 45.7 | 1.54 | 100 |
| His Trap SP FF | 2.64 | 18.23 | 9.23 | 39.01 |

As summarized in Table 5, the $k_{cat}$ value of LOX-S1v1 was increased by 2.4-fold than that of the wild-type LOX. The specific activity of LOX-S1v1 was 1.9-fold increased, the catalytic efficiencies ($k_{cat}/K_m$) was 1.3-fold increased and the half-life of the LOX was increased from 10 min to 38 min. However, the fusion enzymes had the higher $K_m$ value than that of wild-types, suggesting a decrease in substrate affinity after S1v1 peptide fusion.

TABLE 5

Enzymatic properties of the wild-type LOX and the fusion proteins

| Enzyme | Value ± SD | | | | |
|---|---|---|---|---|---|
| | Km (mmol/L) | kcat (S$^{-1}$) | kcat/Km (mmol/S · L) | Specific activity (U · mg$^{-1}$) | half-life ($t_{1/2}$, min) |
| LOX | 0.057 ± 0.0012 | 24.77 ± 0.97 | 434.56.9 ± 3.22 | 32.5 ± 0.34 | 9.4 ± 0.33 |
| LOX-His | 0.055 ± 0.002 | 25.21 ± 1.02 | 458.36 ± 6.73 | 34.5 ± 0.8 | 10.04 ± 0.21 |
| LOX-S1v1 | 0.083 ± 0.002 | 83.2 ± 3.25 | 1002.41 ± 10.32 | 94.3 ± 1.31 | 38.3 ± 2.3 |

Example 3

(1) The nucleotide sequence (as shown in SEQ ID NO. 2) encoding the self-assembling amphipathic peptide (S1v1, amino acids sequence is shown in SEQ ID NO.1) was synthesized and cloned into pET-22b(+) between the restriction EcoRI and NcoI sites for expression, which constructed the recombinant vector pET-22b(+)/S1v1.

(2) The LOX gene (shown in SEQ ID NO. 6) was cloned into the recombinant vector pET-22b(+)/S1v1 at the restriction NcoI and XhoI sites to construct a recombinant plasmid pET-22b(+)/gfp-S1v1.

(3) The recombinant plasmid pET-22b (+)/S1v1-GFP was transformed into host E. coli BL21 (DE3) to construct the recombinant strain E. coli BL21 (DE3) pET-22b (+)/gfp-S1v1.

(4) The recombinant E. coli BL21 (DE3) pET-22b(+)/gfp-S1v1 were inoculated and incubated. The IPTG was concentration of 0.05 mM was added to induced the GFP expression at 20° C. for 24 h. The culture broth was centrifuged. Cells were collected and broke before centrifugation, supernatant was obtained for purification and enzyme analysis.

Figure 4:
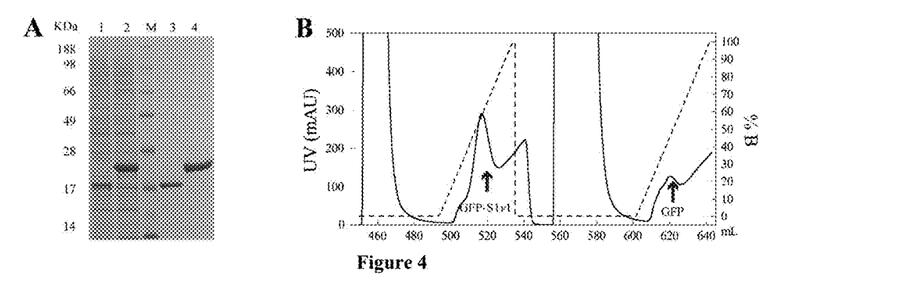
FIG. 4. (A) SDS-PAGE analysis of the purified GFP and GFP-S1v1 and the intracellular expression quantity of GFP and GFP-S1v1. M, molecular mass marker; 1, intracellular soluble of GFP; 2, intracellular soluble of GFP-S1v1; 3, the purified GFP; 4, the purified GFP-S1v1, (B) The Nickel column affinity chromatography of GFP-S1v1 and GFP with His-tag.

On account of the poor expression quantity in this culture condition, the purification yield of GFP with His-tag was only 7.25% while GFP-S1v1 was 56.1% without pretreatment under about 30 mL injection amount. After the purification by nickel affinity chromatography (FIG. 4B), SDS-PAGE analysis showed that the GFP with the His-tag and GFP-S1v1 were purified to homogeneity and the molecular weight were about 27 and 31 kDa, respectively (FIG. 4A). The expression quantity of the fusion proteins were significantly improved than that of wild-types. The fusion proteins GFP were obviously expressed highly than that of the wild-types under the same conditions.

TABLE 4

Purification steps of the GFP from E. coli

|  | GFP | | GFP-S1v1 | |
| --- | --- | --- | --- | --- |
| Enzyme Steps | Crude extract | His Trap SP FF | Crude extract | His Trap SP FF |
| Total protein (mg) | 40.8 | 1.02 | 23.5 | 3.3 |
| Total fluorescence intensity | 338170 | 24527 | 1044235 | 586055 |
| Specific fluorescence intensity (mg$^{-1}$) | 422.32 | 24524 | 44435.53 | 175992.42 |
| Yield (%) | 100 | 7.25 | 100 | 56.1 |

Figure 5:
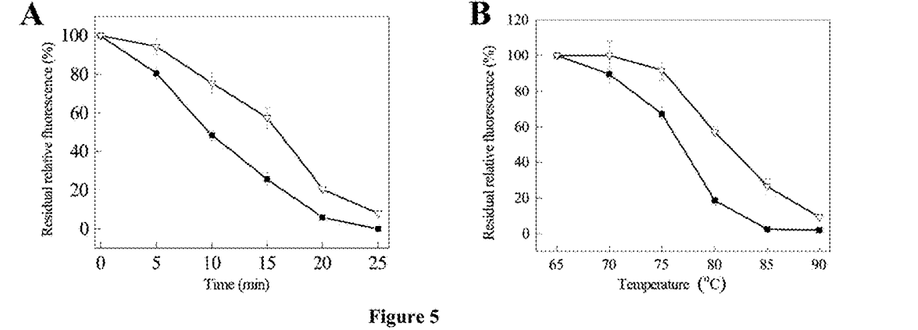
FIG. 5. Thermal stability of GFP and GFP-S1v1. (A) Time-dependent temperature effect on the stability of GFP and GFP-S1v1 at 75° C. The fluorescence at time zero min was taken as 100%. (B) Effect of various temperatures on the stability proteins. The stability was measured by incubating at different temperatures for 5 minutes and the remaining fluorescence was plotted against temperature as function. (Error bar—Standard deviation of three experiments). (■) GFP with His-tag; (▽) GFP-S1v1.

The GFP protein have the clear degradation mechanism and was evaluated to be relatively stable as well as fold very efficiently under different protein denaturation conditions. And herein, the thermal stability of GFP and GFP-S1v1 were measured and compared. In time-dependent assay at 75° C., the thermal inactivating curve of GFP was steeper than that of GFP-S1v1 which indicated fluorescence of GFP was decreased faster than that of GFP-S1v1 over time (FIG. 5A). The residual fluorescence of GFP reduced by half with 10 min when GFP-S1v1 just reduced by a total of 30%. Specifically, the thermal stability was evaluated by incubating both protein samples at temperatures at different temperature for 5 min with approximate protein concentration. As shown in FIG. 5B, the activities of both GFP and GFP-S1v1 were not changed at 65° C. for 5 min, but from 75° C., GFP readily lost its fluorescence as the temperature increases compared to GFP-S1v1. The most obvious differences were at 80° C., GFP-S1v1 had 60% residual fluorescence while GFP had reduced by 80%. In addition, GFP almost lost its whole fluorescence with 5 min over 80° C. However, the residual fluorescence of GFP-S1v1 was about 30% of the original with 5 min heat preservation at 85° C.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method, comprising constructing a recombinant fusion protein comprising a peptide with an amino acid sequence as set forth in SEQ ID NO:1 linked to a protein; purifying by nickel affinity chromatography the fusion protein from culture supernatant using the peptide as a purification tag.

2. A fusion protein comprising:
a self-assembling amphipathic peptide with an amino acid sequence as set forth in SEQ ID NO: 1:
a protein;
wherein the self-assembling amphipathic peptide is linked to the protein;
wherein the protein is a bioactive enzyme;
wherein the protein is an alkaline polygalacturonate lyase (PGL) encoded by a nucleotide sequence as set forth in SEQ ID NO: 4.

* * * * *